United States Patent [19]

Hukuba

[11] Patent Number: 4,458,374
[45] Date of Patent: Jul. 10, 1984

[54] ELECTRIC TOOTH BRUSH HOLDER

[76] Inventor: Hiroshi Hukuba, No. 914-1, Nazukari, Nagareyama-shi, Chiba-ken, Japan

[21] Appl. No.: 361,764

[22] Filed: Mar. 25, 1982

[30] Foreign Application Priority Data

Apr. 6, 1981 [JP] Japan .................................. 56-52140
Oct. 21, 1981 [JP] Japan .................................. 56-167153

[51] Int. Cl.³ ............................................ A46B 13/02
[52] U.S. Cl. ..................................... 15/22 R; 279/28
[58] Field of Search .................. 15/22 R, 22 A, 22 C; 279/28, 29; 310/80; 128/62 A, 52

[56] References Cited

U.S. PATENT DOCUMENTS

| 2,095,956 | 10/1937 | Bess | 15/22 R |
| 2,875,458 | 3/1959 | Tsuda | 15/22 R |
| 3,142,852 | 8/1964 | Phaneuf et al. | 15/22 R |
| 3,168,834 | 2/1965 | Smithson | 15/22 R X |
| 3,196,299 | 7/1965 | Kott | 15/22 R X |
| 3,316,576 | 5/1967 | Urbush | 15/22 R |
| 3,562,566 | 2/1971 | Kircher | 15/22 R X |

FOREIGN PATENT DOCUMENTS 1216838 11/1959 France ............................... 15/22 R Primary Examiner—Edward L. Roberts
Attorney, Agent, or Firm—Koda and Androlia

[57] ABSTRACT

This electric tooth brush holder includes a cylindrical handle portion, and a motor, a drive unit and a cylindrical attachment disposed within said cylindrical handle portion, wherein said attachment is designed to reciprocate within the cylindrical handle portion through said drive unit by the action of said motor and further is provided on its top with a brush holding ring which has been disposed to stand erect normally and permitted to oscillate in the vertical direction.

9 Claims, 35 Drawing Figures

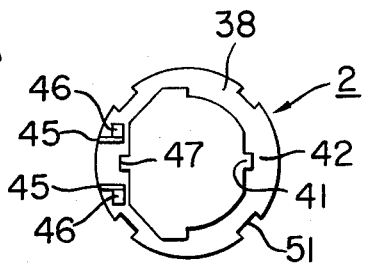
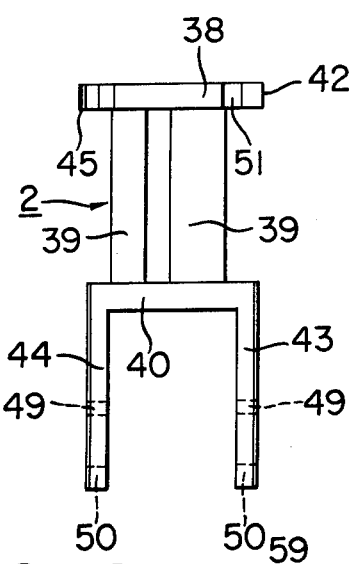
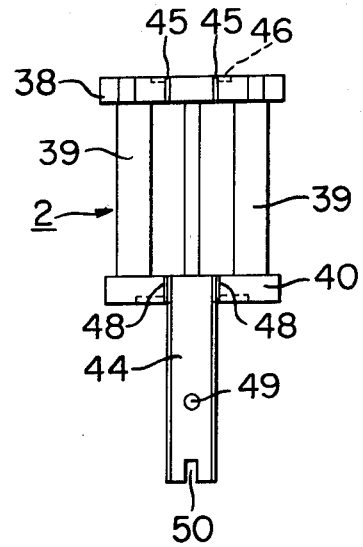
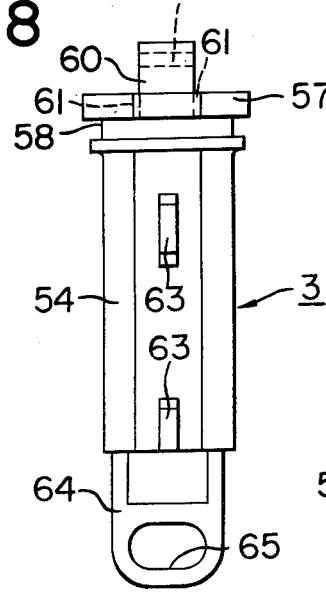
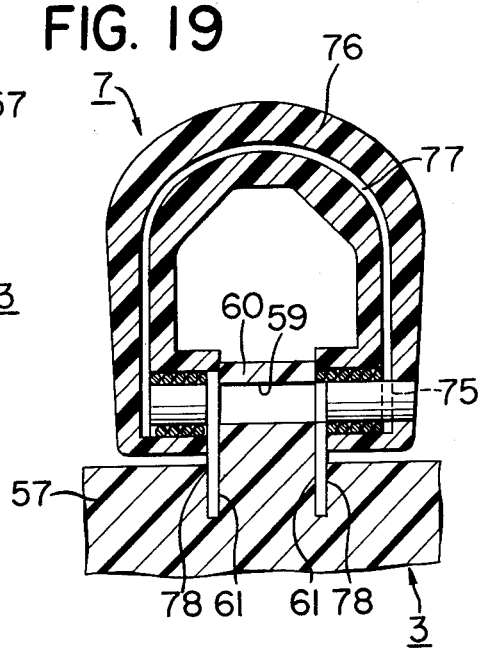

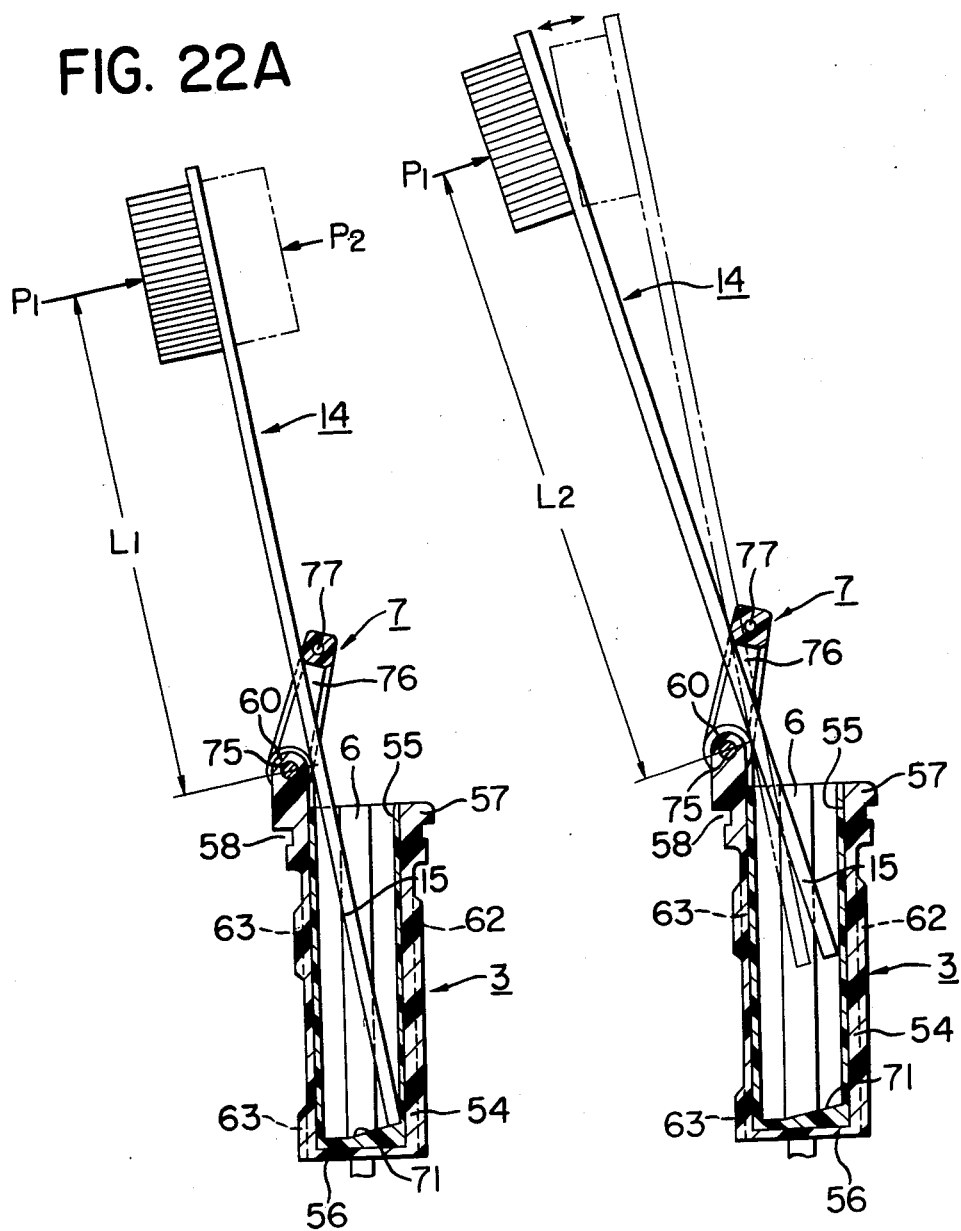

ELECTRIC TOOTH BRUSH HOLDER

BACKGROUND OF THE INVENTION

This invention relates to an electric tooth brush holder.

A tooth brush holder is well known which comprises mounting a commercially available tooth brush detachably on an attachment disposed within a cylindrical handle portion accommodating a motor therein and designed to reciprocate by means of a motor-actuated drive unit (Japanese Patent Publication No. 27372/1967).

However, the prior art tooth brush holder of this type is of various shortcomings: when attaching a tooth brush to a tooth brush holder, one's considerable strength must be put out for forcing the tooth brush in the attachment and pulling it out thereof for the purpose of removing; there is caused a difference in supporting force of the holder depending upon the dimension and configuration of the handle of the tooth brush, for instance, when the handle is thin the supporting force of the holder is so weak that the brush is apt to come out of it; paste is apt to enter into the cylinderical handle portion and solidify to thereby hinder the operation and at the same time saliva enters into the cylindrical handle portion to thereby cause uncleanness; in so far as the user keeps the holder at a fixed position when using it, the tooth brush is held at a fixed position irrespective of unevenness of the teeth so that high teeth thrust into the brush portion while low teeth only contact with the surface of the brush, thereby hindering uniform polish of teeth; and in order to polish the teeth uniformly the user must vary the position of the teeth brush in accordance with the uneven tooth which is substantially impossible.

SUMMARY OF THE INVENTION

It is an object of this invention to provide an electric tooth brush holder which is capable of eliminating the above mentioned shortcomings inherent in the usually known electric tooth brush holders, attaching and removing the tooth brush readily by little force, supporting the handles of various dimensions and configurations by substantially uniform strength to thereby prevent their coming out, and further varying the position of tooth brush attached to the holder so that the tooth brush may contact teeth in substantially uniform manner.

The above object can be achieved by the electric tooth brush holder according to this invention which comprises a cylindrical handle portion, and a motor, a driving member and a cylindrical attachment provided within said cylindrical handle portion, wherein said attachment is designed to reciprocate within said cylindrical handle portion through said drive unit by the action of said motor and further is provided on its top with a brush holding ring which has been disposed to stand erect normally and permitted to oscillate in the vertical direction.

It is another object of this invention to provide a tooth brush holder which is capable of preventing the intrusion of paste and saliva into the cylindrical handle portion to thereby ensure an undisturbed normal operation and keep the general instrument clean.

The above object can be achieved by the embodiment of this invention wherein the gap between the cylindrical handle portion and the cylinderical attachment is covered by a bellows whose one end is attached to the cylindrical handle portion and another end is attached to the cylindrical attachment and further an O ring is attached onto the back of a knob for switch disposed on the outer surface of the cylindrical handle portion so that said O ring may contact slidably with the outer surface of the cylindrical handle portion for sealing purposes.

It is a further object of this invention to provide an electric tooth brush holder whereon said tooth brush is arranged to not rotate but reciprocate covering a fixed stroke in the vertical direction alone and in both the vertical and horizontal directions so that the tooth brush can be moved selectively in conformity with the user's teeth conditions and the like.

The above object can be achieved by the respective embodiments of this invention designed so that a leg portion provided vertically on the bottom of the cylindrical attachment supported movably on an attachment supporter disposed non-rotatably within the cylindrical handle portion, an eccentric body portion secured integrally to a driven gear is fitted in a hole perforated in this leg portion, and this driven gear is engaged with a drive gear mounted on a motor shaft so as to rotate the eccentric body portion when the motor is operated, wherein the one arranged to reciprocate in the vertical direction is designed so that the horizontal dimension of said hole is larger than the diameter of the eccentric body portion while the one arranged to reciprocate in both the vertical and horizontal directions is designed so that said hole is round and its inside diameter is substantially equal to the outside diameter of the eccentric body portion.

It is still a further object of this invention to provide a current tooth brush holder designed so that even when the holding ring located nearest to the lip of the user touches it by mistake during use, the lip is not hurt as well as coming out of the tooth brush can be prevented with certainty.

The above object can be achieved by the embodiment of this invention wherein the holding ring comprises an elastic material made body whose leg portion is pivotally supported on a pivot mounted on the bearing portion of the attachment and a spring embedded in this body and wound around said pivot.

It is another important object of this invention to provide an electric tooth brush holder which is capable of controlling the motor easily during use.

The above object can be achieved by the embodiment of this invention wherein the knob for switch is designed to slide vertically along the outer surface of the cylindrical handle portion.

It is an additional object of this invention to provide an electric tooth brush holder which is not in danger of making the user feel unpleasant by minimizing the vibration and noise produced by the operation of the motor and its drive unit.

The above object can be achieved by the embodiment of this invention wherein the upper portion of the attachment supporter on which the cylindrical attachment is movably supported is disposed within the cylindrical attachment by the aid of an elastic ring, while the motor is supported within the cylindrical handle portion by an elastic material-made motor supporter.

BRIEF DESCRIPTION OF THE DRAWING

FIGS. 17A, 17B and 17C are each a plan view, a front view and a left side view of the attachment supporter of the tooth brush holder illustrated in FIG. 9.

FIG. 18 is a front view of the attachment of the tooth brush holder illustrated in FIG. 9.

FIG. 19 is an enlarged vertical sectional front view of the tooth brush holding ring of the tooth brush holder illustrated in FIG. 9.

FIGS. 22A and 22B are each a vertical sectional front view illustrating the state where the tooth brush has been inserted, in a different manner, into the attachment used as usual in the tooth brush holder of FIG. 9.

Three embodiments of electric tooth brush holder according to this invention will be explained hereinafter with reference to the accompanying drawing. In this connection, it is to be noted that same reference numerals will be attached to same structures in the respective embodiments.

DETAILED DESCRIPTION OF THE INVENTION

Figure 1:
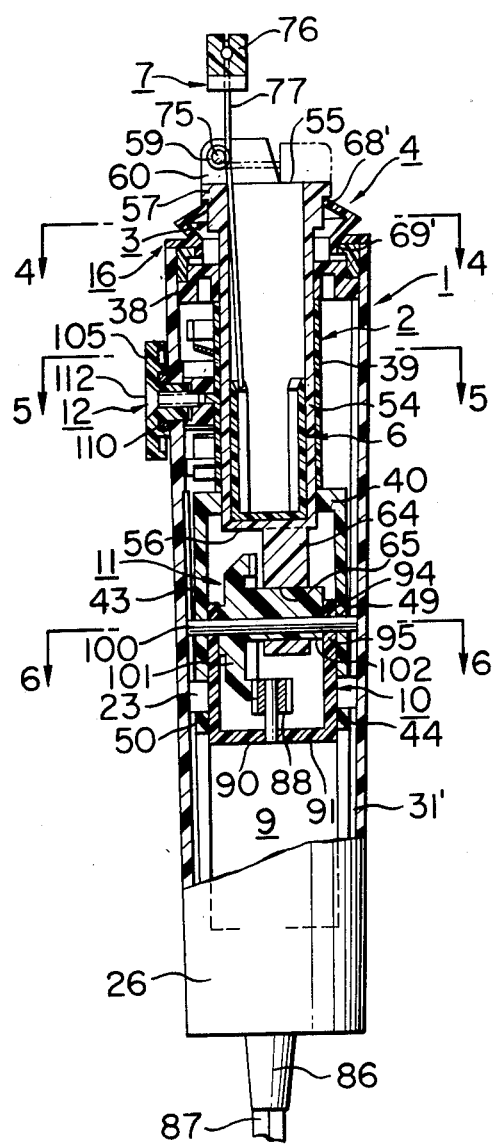
FIG. 1 is a partially vertical sectional front view of the first embodiment of the electric tooth brush holder according to this invention.
Figure 2:
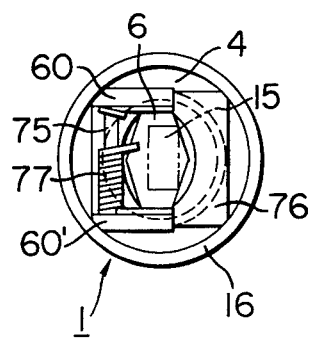
FIG. 2 is a plan view of the electric tooth brush holder of FIG. 1 with the holding ring brought down.
Figure 4:
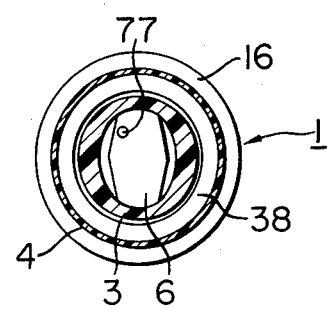
FIG. 4 is a sectional view of FIG. 1 taken on the line 4—4 and viewed in the direction of the arrow.
Figure 3:
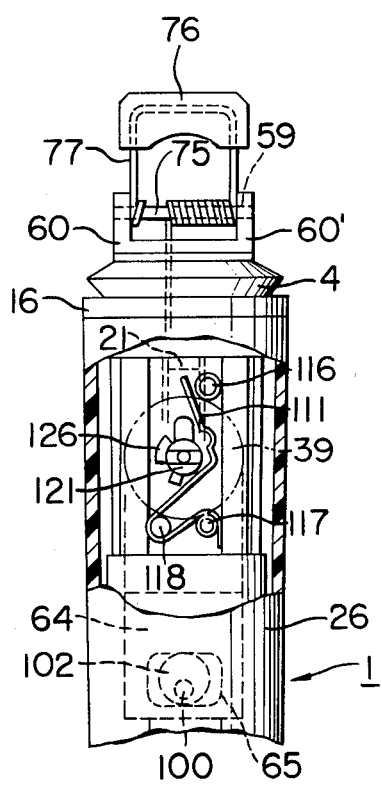
FIG. 3 is a left side view illustrating the holding body of the tooth brush of FIG. 1 in partially cutaway manner.

In the first embodiment illustrated in FIG. 1 to FIG. 6, 1 denotes a cylindrical handle portion, and 26 denotes its body wherein the bottom portion is provided with a hole, the diametrically confronting inner walls are provided with a pair of protrudent ribs 30, 30 and a pair of protrudent ribs 30', 30' both extending from the bottom up to the vicinity of the top portion, and further the inner walls making a right angle with these ribs 30, 30 and 30', 30' are also provided with a pair of longitudinal ribs 31, 31 and a pair of longitudinal ribs 31', 31' as mentioned above.

In the upper end opening of the body 26 there is closely fitted a skirt portion of a holding ring 16, and this skirt portion is provided at its upper end with a circular flange 20.

Reference numeral 2 denotes an attachment supporter disposed in the handle portion body 26 downwards of the holding ring 16, said attachment supporter being comprised of integrally coupled upper flange 38, intermediate sleeve 39 and lower flange 40. On the outer peripheral surface of the upper flange 38 there is provided a rib 21 at a place confronting each groove formed between ribs 30, 30 and 30', 30' within the handle portion body, and this rib 21 is fitted in said groove. The lower flange 40 is provided with hanging leg portions 43 and 44, and their lower ends engage ribs 30 and 30' and 31 and 31' within the handle portion body 26 respectively so as to be held there. And, a hole 49 is perforated in the middle of leg portions 43 and 44 and a hole 50 is perforated in the vicinity of the lower end thereof respectively.

Figure 5:
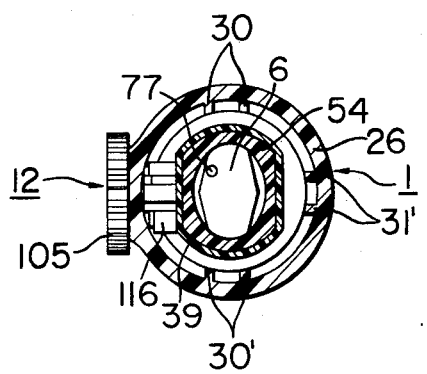
FIG. 5 is a sectional view of FIG. 1 taken on the line 5—5 and viewed in the direction of the arrow.
Figure 6:
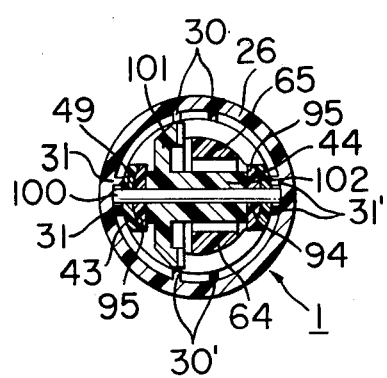
FIG. 6 is a sectional view of FIG. 1 taken on the line 6—6 and viewed in the direction of the arrow.

Reference numeral 3 denotes an attachment fitted slidably within the supporter 2. This attachment has a cylindrical body 54 whose upper part is provided with an opening 55 and whose lower part has been closed with a bottom plate 56. On a circular flange 57 located at its upper end there are mounted a pair of bearing portions 60 and 60, each having a horizontal hole 59, and the bottom plate 56 is provided with a hanging leg portion 64 in which a horizontal long hole 65 is perforated. The outer periphery of the body 54 fitting slidably on the supporter 2 for the attachment 3, as seen from FIG. 5, is shaped plane at diametrically confronting portions so that the body does not rotate when the attachment 3 moves vertically within the supporter 2. Further, on the bottom plate 56 within the body 54 there is fitted a protective cylinder 6 made from an elastic material such as rubber, soft plastics or the like for the purpose of protecting the fore end of the handle 15 of the tooth brush 14.

Reference numeral 4 denotes a water proofing bellows made from an elastic body such as rubber, soft plastics or the like, wherein an upper opening edge 68 is closely fitted to a lower peripheral edge of the flange 57 of the attachment 3, a circular flange 20 of the holding ring 16 is closely fitted in a circular groove provided in the vicinity of the lower end of the lower peripheral edge, and a lower end peripheral edge is seated on a top peripheral edge of the supporter 2.

Reference numeral 7 denotes a holding ring, wherein the other end of an adverse U-shaped spring 77, whose one end has been secured to a pin 75 attached to the bearing portions 60 and 60' of the attachment 3, is wound around the pin 75 and then its fore end is hung down in the attachment 3 in order to bias the spring 77 by its elastic force so that the spring 77 may be always held erect, and further a holding means 76 is mounted on the upper edge horizontal part of this spring 77, said holding means 76 being made from an elastic material such as soft plastics, rubber or the like which has a relatively high friction coefficient.

Reference numeral 10 denotes a drive unit supporter wherein a base plate 91 is secured to the top part of a motor 9, said base plate having a hole 90 which the rotary shaft of said motor 9 fits in and protrudes beyond. On the upper peripheral edge portion of the base plate 91 there are provided a pair of stand plates 95 which abuts, at its outside, against the inside of leg portions 43 and 44 of the lower flange of the supporter 2 and further have a hole 94 perforated at the place confronting the hole 49. On the lower outer peripheral portion of this stand plate 95 there is provided a rib 23 which penetrates the hole 50 perforated in the leg portions 43 and 44 and fits in a groove formed between ribs 31, 31 and 31', 31'.

A drive shaft 100 is supported by the hold 49 perforated in leg portions 43 and 44 and the hole 94 perforated in the stand plate 95, and is further provided with a bevel gear 101 engaging a pinion 88 and a drive unit 11 having an eccentric body portion 102 fitted slidably in the long hole 65 of the attachment 3.

Figure 7A:
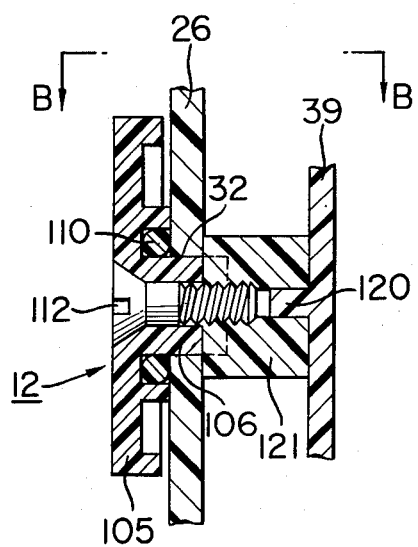
FIG. 7A is an enlarged vertical sectional view of the switch portion of the tooth holder illustrated in FIG. 1.
Figure 7B:
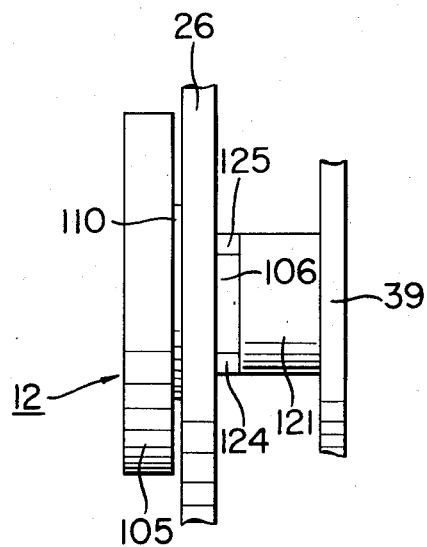
FIG. 7B is a view of FIG. 7A viewed in the direction of the arrow along the line B—B.

Reference numeral 12 denotes a switch attached to the handle body 26. This switch mechanism will be explained with reference to FIG. 7 and FIG. 8.

Reference numeral 105 denotes a knob. The boss portion 106 of said nob is supported rotatably in a longitudinal hole 32 perforated in the wall surface of the handle body 26, and an O ring 110 is provided around the boss portion 106 to thereby closely seal the gap between the boss portion and the wall surface of the body 26.

Figure 8A:
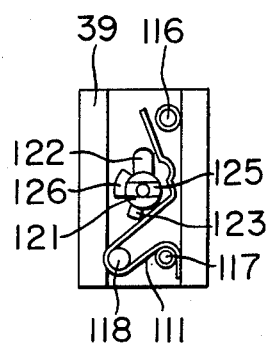
FIGS. 8A and 8B are views showing the operating state of mainly the contact portion of the tooth brush of FIG. 1.
Figure 8B:
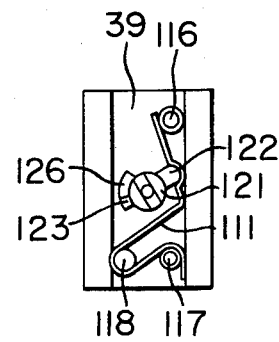

On the other hand, on the plane surface of the sleeve 39 confronting the switch 12 there are erectly provided upper and lower fixed contact pins 116 and 117. One end of a movable contact mounting member 111 is wound around the lower contact pin 117 and the other end thereof extends up to the vicinity of the upper contact pin 116 through a guide pin 118 provided on the side plate 39 (FIG. 8A).

On the surface of the side plate 39 substantially in the middle of pins 116, 117 and 118 there is erectly provided a pivot pin 120 on which a sleeve 121 is rotatably fitted.

And, a push piece 122 and a stopper piece 123 are provided in projecting manner at the substantially diametrically confronting places on the peripheral surface of this sleeve 121.

A radial groove 124 is perforated in the end surface of the boss portion 106, while the end surface of the sleeve 121 confronting the above surface is provided with a rib 125 to be fitted in said groove 124. After having been fitted up, they are screwed with a set screw 112. The rib 125 is longer than the diameter of the longitudinal hole 32 in order to hold the position of the sleeve 121.

In the normal state of this switch 12, as shown in FIG. 8A, the fixed contact pin 116 is separated from the movable contact mounting member 111 and the circuit is open. When closing the circuit, the knob 105 is turned to thereby turn the sleeve 121 so that the push piece 122 of the sleeve 121 transfers the movable contact 111 to the position indicated in FIG. 8B. Thus, the circuit is closed and consequently a stopper piece 123 engages a projecting stopper 126 provided on the side plate and stops.

The operation of this first embodiment is exactly identical with that of the second embodiment. Therefore, it will be described afterwards in explaining the second embodiment.

Next, explanation will be made on the second embodiment of this invention illustrated in FIG. 7 to FIG. 20. However, explanation on the same matters as the first embodiment will be omitted, and the matters different therebetween will be mainly explained.

Figure 16:
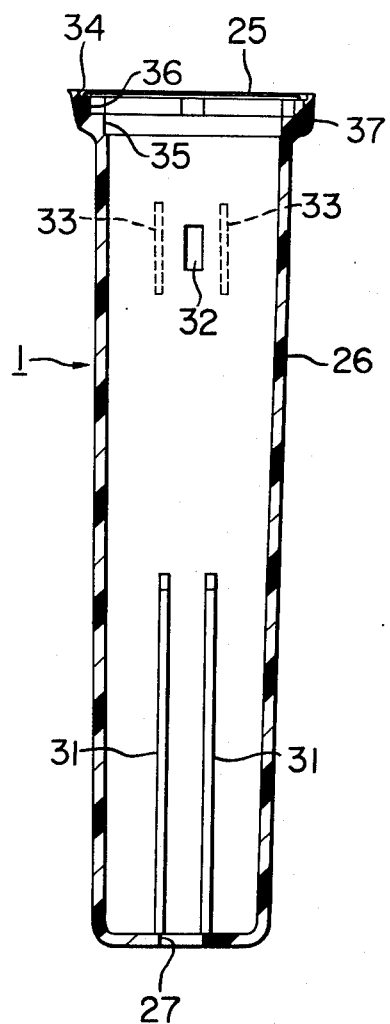
FIG. 16 is a vertical sectional front view of the cylindrical handle body of the tooth brush holder illustrated in FIG. 9.
Figure 15:
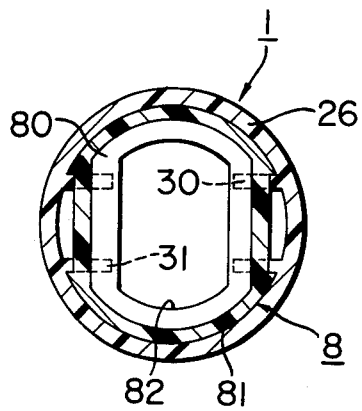
FIG. 15 is an enlarged sectional view of FIG. 10 taken on the line 15—15 and viewed in the direction of the arrow.

Referring to FIG. 16, in particular, a handle portion 1 is made from a resin, for instance, such as ABS or the like. The top opening portion of a body 26 is provided with a stepped mouth portion comprising a large hole 34, a small hole 35 and an intermediate level portion 37. And, the upper surface of the level portion 37 is provided with a circular rib 25, and the upper inner peripheral wall of the small hole 35 is provided with a plurality of radially outward recesses 36. The bottom of the body 26 is provided with a hole 27, and further each pair of longitudinal ribs 30 and 31 which are of fixed height from the bottom are provided at the diametrically confronting places on the inner wall of the body 26. And, a longitudinal hole 32 is perforated in the upper part of the outer wall making a right angle with the ribs 30 and 31, and longitudinal slits 33 are formed on the outer surface on both sides of this hole.

Figure 12:
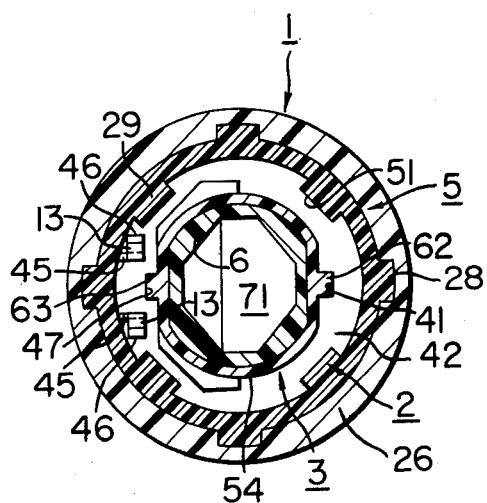
FIG. 12 is an enlarged sectional view of FIG. 10 taken on the line 12—12 and viewed in the direction of the arrow.

In the small hole 35 there is closely fitted the skirt portion of an elastic supporting ring 5 whose upper outer periphery, as shown in FIG. 12, is provided with several ribs 28 which are closely fitted in recesses 36 of the small hole 35, further whose inner periphery is provided with several ribs 29.

Figure 13:
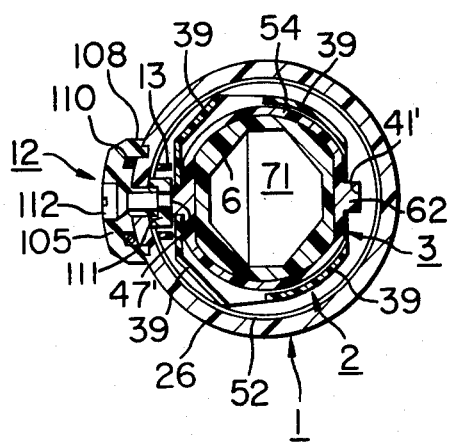
FIG. 13 is an enlarged sectional view of FIG. 10 taken on the line 13—13 and viewed in the direction of the arrow.
Figure 14:
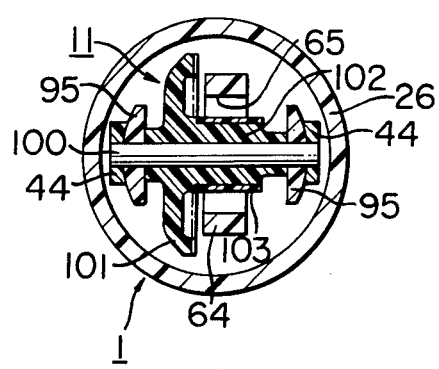
FIG. 14 is an enlarged sectional view of FIG. 10 taken on the line 14—14 and viewed in the direction of the arrow.

Referring to FIG. 17, in particular, an attachment supporter 2 is made from a resin, for instance, such as polyacetal or the like, and its outer peripheral surface as a whole is designed to form a space 52 in conjunction with the inner peripheral surface of a handle portion 1. The outer periphery of a circular upper flange 38 supported by a supporting ring 5 is provided with recesses 51 in which inner ribs 29 are fitted. A circular lower flange 40 attached to this flange 38 by means of several side plates 39 is provided with recesses 41' and 47' at the places opposite to recesses 41 and 47 of the flange 38 (FIG. 13). The flange 38 is provided with a segment portion 42 which fits in longitudinal grooves formed between ribs 29 of the supporting ring 5 for supporting the supporter 2 at a predetermined position relative to the handle portion 1, and the lower flange 40 is provided with protrudent leg portions 43 and 44. Two slits 45 are perforated in the one side outer periphery of the segment portion 42 of the upper flange 38, and dents 46 are provided on the top surface of the flange 38 connected making a right angle with the top portions 45 of these slits. Further, the inner periphery of the upper flange 38 is provided with recesses 41 and 47 on the same diametrical line thereof. The lower flange 40 is provided with a slit 48 at the position opposite to the slit 45, a hole 49 is formed in the middle of leg portions 43 and 44, and a recess 50 is formed at the lower end thereof respectively.

Figure 10:
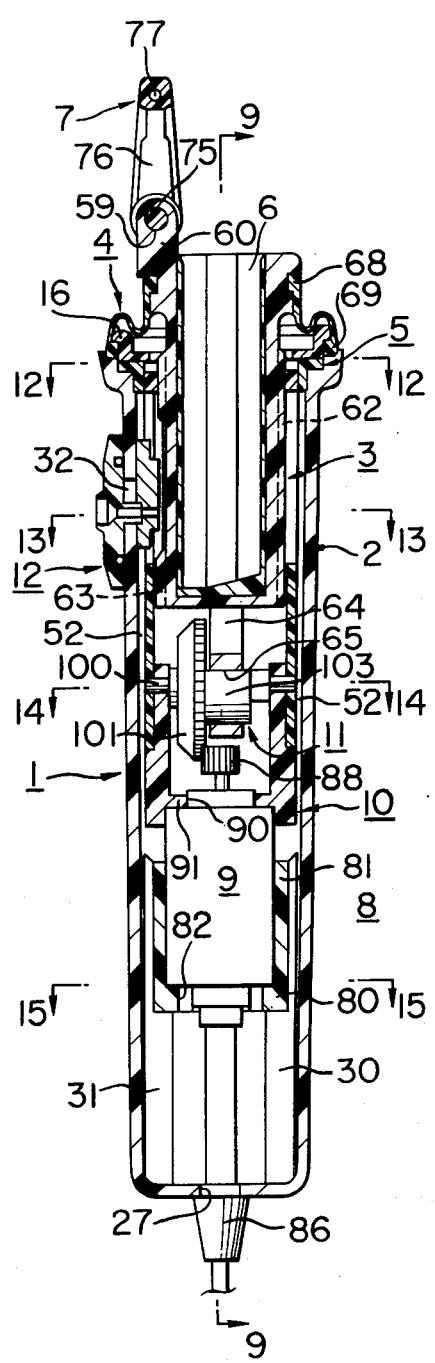
FIG. 10 is a sectional view of FIG. 9 taken on the line 10—10 and viewed in the direction of the arrow.
Figure 11:
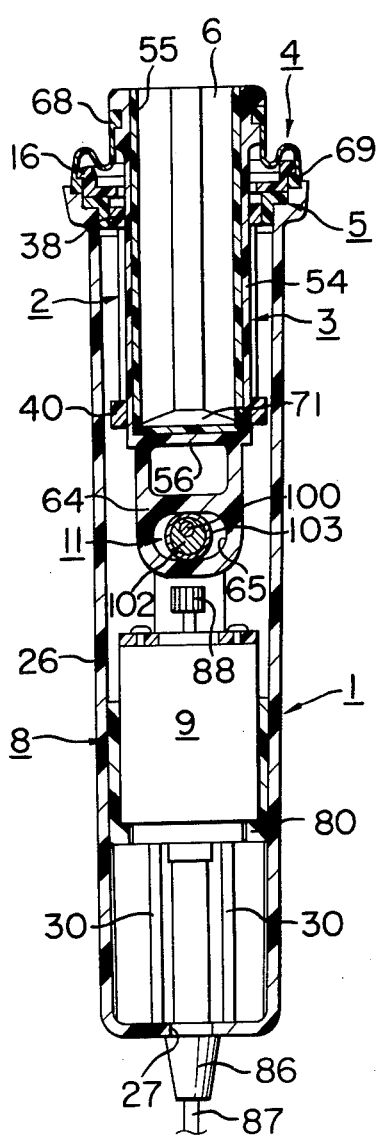
FIG. 11 is a sectional view of FIG. 10 taken on the line 11—10 and viewed in the direction of the arrow.

Referring to FIG. 11 and FIG. 18, in particular, an attachment 3 has a cylindrical body 54 made from a resin, for instance, such as nylon or the like, its top portion is provided with an annular flange 57, an annular groove 58 is formed thereunder, a bearing portion 60 with horizontal holes is provided erectly in the flange 57, and holes 61 are perforated in the flange 57 on both sides of this bearing portion 60. On the outer periphery of the body 54 opposite to the recesses 41 and 47 of the supporter 2 there are provided longitudinal ribs 62 (FIG. 10) and 63 which slidably fit in said recesses, and the rib 63 is notched in the middle and divided into two upper and lower portions.

An elastic material-made bellows 4 is provided with inward upper and lower circular flanges 68 and 69. The upper flange 68 is closely fitted in the circular groove 58 of the attachment 3, and the lower flange 69 is closely fitted in the opening portion 34 of the handle portion 1. Thereafter, both flanges are secured rigidly to the handle portion 1 by virtue of a holding ring 16 closely fitted in the opening portion 35 of the handle portion 1. The upper opening portion of the handle portion 1 is thus closed up by this bellows 4.

The bottom plate 71 of an elastic material-made tooth brush receiving cylinder 6 fitted rigidly in the attachment 3 is a slope rising gradually from the side of the bearing portion 60 of the attachment 3 to the side opposite thereto, and a chamber defined therewithin is octagonal in section.

Figure 9:
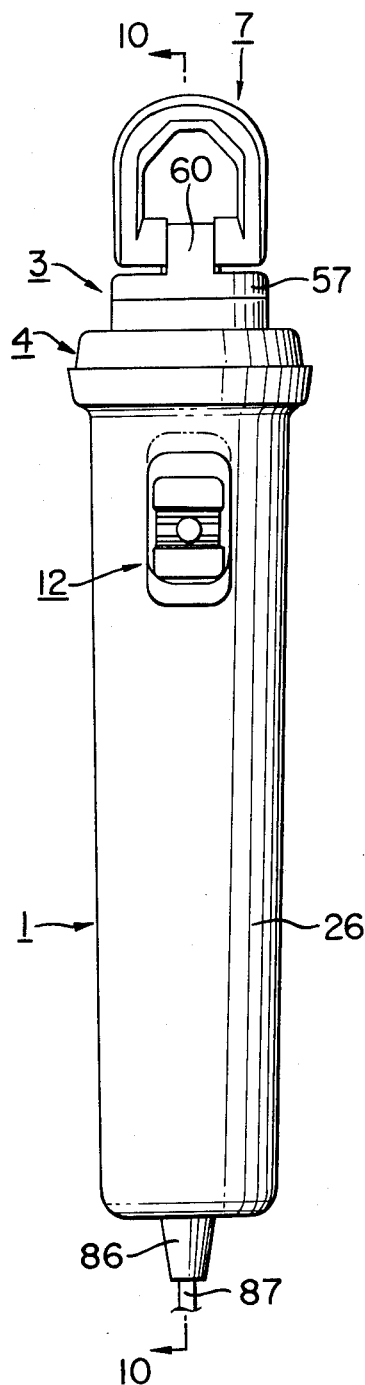
FIG. 9 is an elevational view of the second embodiment of the electric tooth brush holder according to this invention.

Referring to FIG. 19, in particular, an elastic material-made holding ring 7 has a body 76 whose leg portion has been pivotally supported on a bearing portion 60 of an attachment 3 by means of pin 75. In this body 76 there is embedded a spring 77. The lower part of said spring is wound around the pin 75 and thereafter its fore end 78 projects to the outside and fits in a hole 61 perforated in a circular flange 57 of the attachment, thereby biasing the ring 7 so as to keep holding its erect position as shown in FIG. 9 and FIG. 10.

A motor supporter 8 made from an elastic material has an outer periphery fitted on a lower inner periphery of a handle portion 1 and is provided with a bottom plate 80 having a hole 82 at the bottom of a cylindrical portion 81 having an inner periphery for accommodating a motor 9. This bottom plate 80 is carried on ribs 30 and 31 provided on the lower portion of the handle portion 1, thereby supporting the motor 9.

Figure 20A:
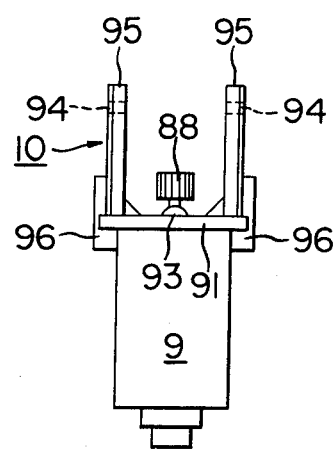
FIGS. 20A and 20B are each a front view and a plan view of the drive unit supporter of the tooth brush holder illustrated in FIG. 7.
Figure 20B:
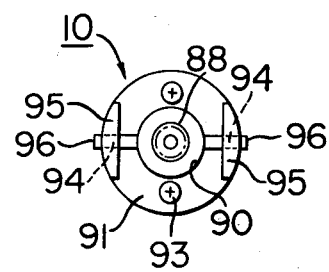

Referring to FIG. 20, in particular, 10 denotes a drive unit supporter wherein a base plate 91 is secured to the top portion of a motor 9 by means of a set screw 93, said base plate being provided with a hole 90 through which the head of the motor 9 fits and then protrudes. Hanging plates 96 are provided connecting stand plates 95 mounted on the peripheral edge of the base plate 91. The top portions of these hanging plates 96 are fitted in recesses 50 at the lower ends or ribs 43 and 44 of the supporter 2 and thus are located.

As an idle ring 103 is fitted outwardly on an eccentric body portion 102 and idles on the body portion 102 and long hole 65, the output can be improved and noise can be decreased.

Figure 21A:
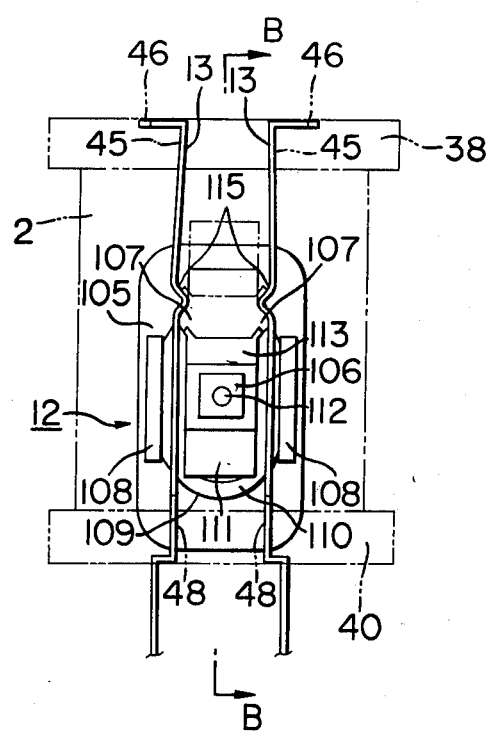
FIG. 21A is an enlarged front view showing the attached state of the switch for use in the tooth brush holder illustrated in FIG. 9.

Referring to FIG. 21, in particular, a switch 12 is attached to the body 26 of a handle portion 1 and located in such a manner that a projecting square pillar 106 provided at the back of a knob 105 curved like the outer periphery of the body 26 is vertically slidably fitted in a longitudinal hole 32 perforated in the body 26 (FIG. 10) as well as ribs 108 provided on both sides of the square pillar 106 are likewise slidably fitted in longitudinal slits disposed on both sides of the longitudinal hole 32. In the back of the knob 105 there is perforated a substantially elliptical groove 109 passing through the middle portion of square pillar 106 and rib 108. And, an O ring 110 is disposed in this groove 109 and said ring 110 abuts on the surface of the body 26 for the purpose of sealing up. A non-electroconductive material-made movable contact mounting member 111 fits to the square pillar 106 by the aid of a square hole provided at the back of said member 111, and is secured to the knob 105 by means of a set screw 112. And, this movable contact mounting member 111 is provided on both sides thereof with projections 107, and a movable contact 113 is wound around the halfway of the slope of one projection.

Reference numeral 13 denotes a pair of fixed contacts made from an electroconductive material which are to be disposed in the circuit of a motor 9. The upper end straight portions of said fixed contacts are fitted in slits 45 perforated in the upper flange 38 of a contact holder 2, the bent portions thereof are supported on dents 46, and the lower ends are fitted in slits 48 of the lower flange 40 and held there. Inside the confronting contracts 13 there is formed a projection 115 which engages the projection 107 of the movable contact mounting member 111. In the open position indicated with a solid line in FIG. 19A the projection 107 engages the lower slope of the projection 115 so as to disconnect contacts 13 and 113, while in the close position indicated with a chain line the project 107 engages the upper slope of the projection 115 so as to connect the contact 13 with the contact 113.

Next, explanation will be made on how to use the tooth brush holder according to this invention mainly with reference to FIG. 22. In the operation of attaching a tooth brush 14 to a holder, a tooth brush holding ring 7 pivotally connected to an attachment 3 is laid down against the force of a spring 77 as shown with a chain line in FIG. 1 and FIG. 2, and then a handle 15 of the tooth brush 14 is inserted through this ring 7 deeply in a brush receiving cylinder 6, thereby releasing the ring 7. Hereat, the ring 7 is allowed to restore its original upright position by the force of the spring 77. Thereat, the ring 7 holds the upper portion of the handle 15 so that the rear end of the teeth brush 14 moves substantially until it engages the inside surface of the receiving cylinder 6 as shown with a solid line in FIG. 22A and thus holds the tooth brush 14 at this place.

Figure 21B:
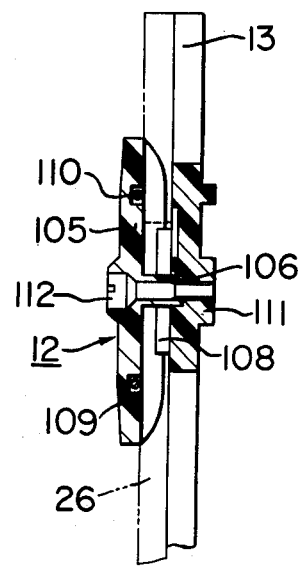
FIG. 21B is a sectional view of FIG. 21A taken on the line B—B and viewed in the direction of the arrow.
Figure 23:
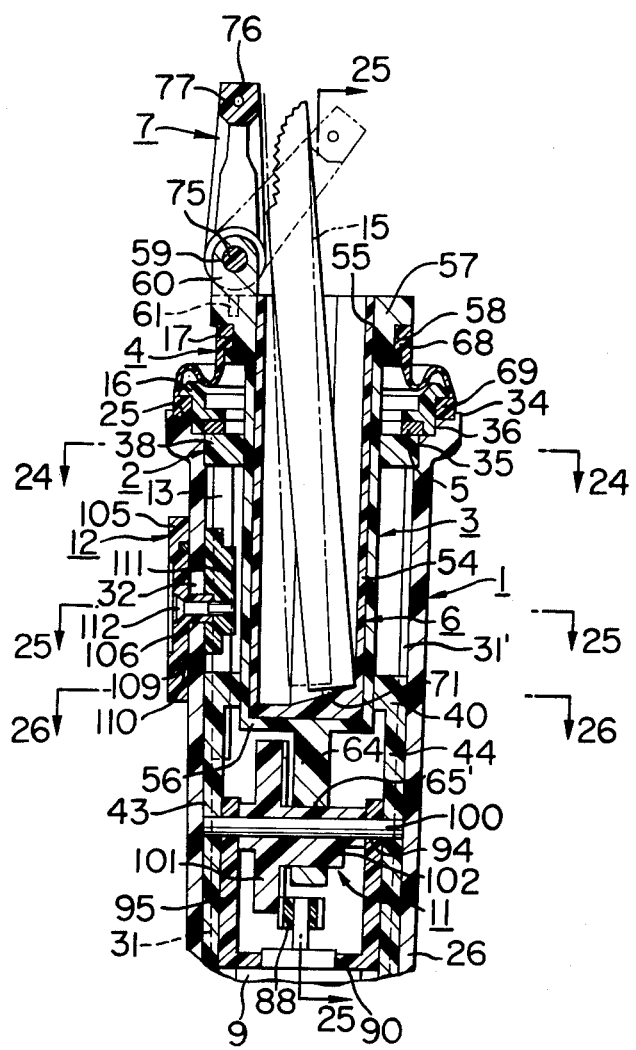
FIG. 23 is a partially vertical sectional front view of the second embodiment of the electric tooth brush holder according to this invention.
Figure 24:
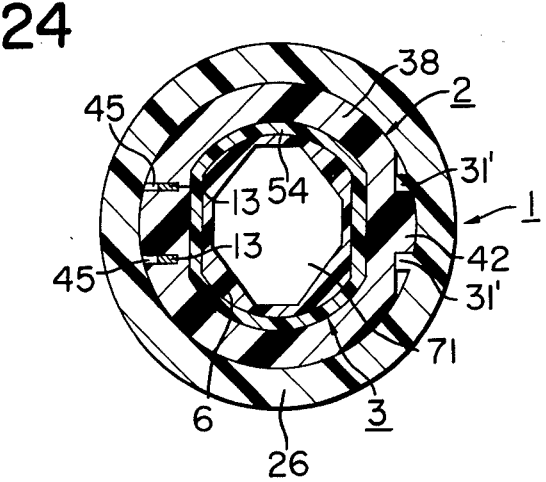
FIG. 24 is an enlarged sectional view of FIG. 23 taken on the line 24—24 and viewed in the direction of the arrow.
Figure 25:
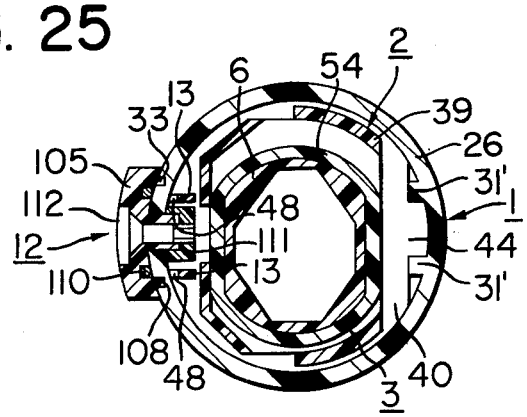
FIG. 25 is an enlarged sectional view of FIG. 24 taken on the line 25—25 and viewed in the direction of the arrow.
Figure 26:
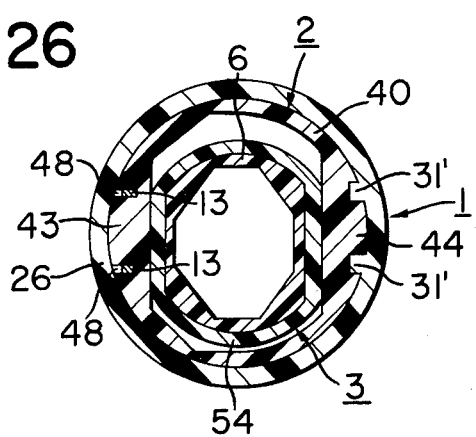
FIG. 26 is an enlarged sectional view of FIG. 24 taken on the line 26—26 and viewed in the direction of the arrow.
Figure 27:
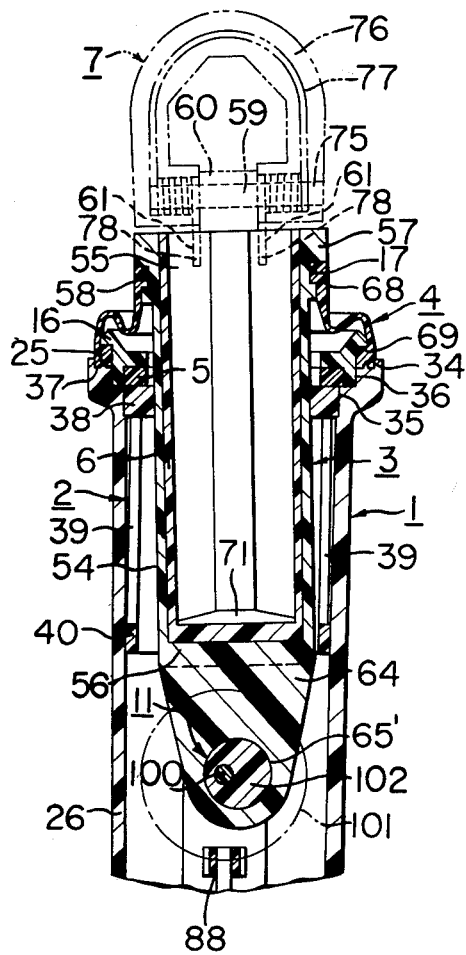
FIG. 27 is a sectional view of FIG. 24 taken on the line 27—27 and viewed in the direction of the arrow.

Thereafter, the knob 105 of a switch 12 is moved at the place indicated with a chain line in FIG. 21B with the teeth brush 14 in one's mouth. Consequently, the circuit of a motor 9 is closed and the motor 9 rotates, whereby the eccentric body portion 102 of a drive unit 11 is rotated through gears 88 and 101. In concert with this, the attachment 3 and the brush receiving cylinder 6 inserted thereinto reciprocate vertically. The tooth brush 14 acts just in concert with this reciprocating motion, thereby brushing one's teeth.

As is evident from the above description, this embodiment is easier to operate than the first embodiment because the former is designed so that the motor 9 is started or stopped by the knob 105 reciprocating vertically along the wall surface of the handle body 26 while the latter is designed so that the motor 9 is started or stopped by the rotation of the knob 105.

FIG. 22B illustrates with a solid line the case where the handle 15 of the tooth brush 14 is inserted more shallowly than the case of FIG. 22A when using the brush holder as mentioned above. As a result of this, the distance L1 between the supporting point and the application point of pressure P1 in the case of FIG. 22A becomes smaller than said distance L2 in the case of FIG. 22B.

Due to this there takes place a phenomenon that even when pressure P1 of the same magnitude is applied on teeth during use, the tooth brush 14 is kept in situ in the case of FIG. 22A, whereas the tooth brush 14 moves from the position indicated with a solid line to that indicated with a chain line and returns to the position indicated with a solid line again when the pressure is released. It is needless to say that if the pressure P1 is more increased, the tooth brush 14 in FIG. 22A will also make the same movement as shown in FIG. 22B. However, it is conceivable that in the case of FIG. 22A where the handle 15 reaches the bottom plate 71 of the brush receiving cylinder 6, the pressure required for said movement will become considerably higher than that employed in the case of FIG. 22B.

Accordingly, it may be said from the above mentioned that even when the user holds the tooth brush at a fixed position relative to teeth, the brush portion retreats and advances automatically in accordance with the unevenness of teeth and thus it becomes easier to brush the teeth uniformly.

Further, when the brush portion is placed in the opposite direction as indicated with a chain line in FIG. 22A, the tooth brush 14 is scarcely moved even by the pressure P2 applied on the tooth brush portion because the lower end of the handle 15 is held by the bottom inner wall surface of the brush receiving cylinder 6.

Due to this, it becomes possible for the user to control the pressure applied on the teeth appropriately in the manner of changing the degree and direction of insertion of the tooth brush depending on the mouth conditions and the places to be brushed.

Next, explanation will be made on the third embodiment of this invention illustrated in FIG. 23 to FIG. 28.

In this connection, it is to be noted that as this embodiment is similar to the above mentioned second embodiment, the explanation on the same parts will be omitted and the different parts will be mainly explained hereinafter.

The first point of difference is that a circular rib 17 is provided in the circular groove 58 of the attachment 3, whereby engagement of the bellows 4 with the upper flange 68 is made more watertight.

Figure 28:
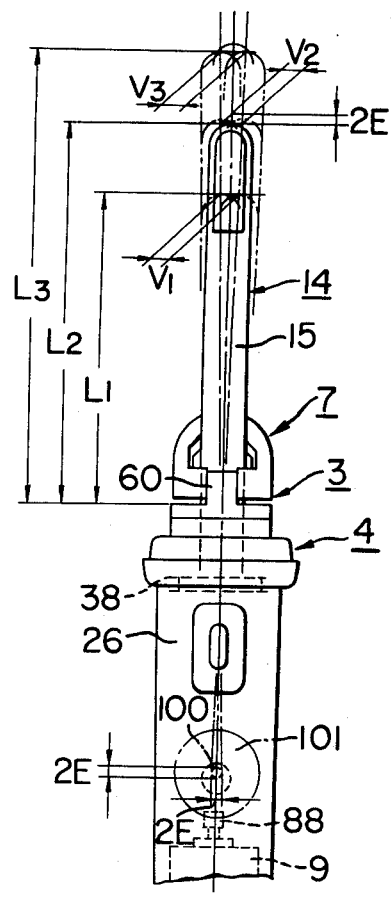
FIG. 28 is a vertical sectional front view illustrating the state where the tooth brush has been inserted, in a different manner, into the attachment used as usual in the tooth brush holder of FIG. 23.

Next, the second point of difference is that the upper flange 38 of the attachment supporter 2 is loosely fitted in the small hole 35 of the handle body 26 to thereby form a fine gap between both surfaces, and a circular hole 65' perforated in the leg portion 64 of the attachment 3 is made in a round shape which is different from that of the hole 65 in the second embodiment. This permits the tooth brush 14 to make the following movement. In this embodiment, when the eccentric amount of the eccentric body portion 102 against the drive shaft 100 is E, the center of the eccentric body portion 102, as shown in FIG. 28, shifts with a stroke 2E reciprocally in both longitudinal and horizontal directions every rotation thereof.

This stroke 2E permits the tooth brush 14 to move vertically with a stroke 2E as well as oscillate horizontally with amplitude V. And, this amplitude V varies depending on the projecting amount L of the tooth brush 14 from the brush receiving cylinder. When this projecting amount is minimum L1, the amplitude V1 is also minimum. As the projecting amount increases from L1 to L2 and L3, the amplitude also increases from V1 to V2 and V3, but this amplitude V sometimes decreases due to the resistance within the user's mouth. However, the amount of vertical movement is changeless and always kept 2E. Accordingly, each part of the tooth brush 14 makes an elliptical motion whose one diameter is 2E and the other diameter is V or makes a circular motion (when 2E is equal to V). As is clear from the above mentioned, this embodiment makes it possible to change the pattern of motion of the tooth brush by controlling the degree of insertion thereof.

Although a particular preferred embodiment of the invention has been disclosed in detail for illustrative purposes, it will be recognized that variations or modifications of the disclosed apparatus, including the arrangement of parts, lie within the scope of the present invention.

What is claimed is:

1. An electric tooth brush holder including a cylindrical handle portion, and a motor, a drive unit and a cylindrical attachment disposed within said cylindrical handle portion for containing a handle of a toothbrush, wherein said attachment is reciprocated within the cylindrical handle portion by said drive unit by the action of said motor and a brush holding ring rotatably coupled to said cylindrical attachment for rotation from a horizontal to a vertical position, said brush holding ring being biased to stand vertically and permitted to oscillate in the vertical direction whereby said brush holding ring cooperates with said cylindrical attachment to hold said toothbrush when said toothbrush is inserted through said brush holding ring and into said cylindrical attachment.

2. An electric tooth brush holder according to claim 1 wherein the opening between the cylindrical handle portion and the cylindrical attachment is covered water-tightly by a bellows whose one end is attached to the cylindrical handle portion and another end is attached to the cylindrical attachment, and further an O ring is attached onto the back of a knob for a switch disposed on the outer surface of the cylindrical handle portion so as to contact said O ring slidably with the outer surface of the cylindrical handle portion.

3. An electric tooth brush holder according to claim 2 wherein the knob for switch is designed to slide vertically along the outer surface of the cylindrical handle portion.

4. An electric tooth brush holder according to claim 1 wherein the cylindrical attachment is supported movably on an attachment supporter disposed non-rotatably within the cylindrical handle portion.

5. An electric tooth brush holder according to claim 4 wherein the cylindrical attachment is provided at its bottom portion with a hanging leg portion with a hole and the drive unit comprises locking an eccentric body portion to a driven gear, said driven gear engaging a drive gear secured to a motor shaft, said eccentric body portion fitting in the hole perforated in the leg portion of the attachment.

6. An electric tooth brush holder according to claim 4 wherein the motor is supported on a motor supporter made from an elastic material, and further the upper portion of the attachment supporter is attached to the cylindrical handle portion by the aid of an elastic ring.

7. An electric tooth brush holder according to claim 1 wherein the tooth brush holding ring comprises an elastic material-made body having a leg portion which is pivotally supported on a pivot mounted on a bearing portion of the attachment and a spring embedded in said body and wound around said pivot.

8. An electric tooth brush holder according to claim 7 wherein the hole perforated in the leg portion of the cylindrical attachment has a vertical dimension substantially equal to the diameter of the eccentric body portion and a horizontal dimension greater than the diameter of the eccentric body portion, whereby the attachment is permitted to reciprocate vertically within the attachment supporter in concert with the rotation of the eccentric body portion.

9. An electric tooth brush holder according to claim 7 wherein a hole perforated in the leg portion of the cylindrical attachment has a round inside diameter substantially equal to the inside diameter of the eccentric body portion, whereby the attachment is permitted to reciprocate within the attachment supporter in the vertical as well as horizontal directions in concert with the rotation of the eccentric body portion.

* * * * *